United States Patent [19]
Park et al.

[11] Patent Number: 5,750,585
[45] Date of Patent: May 12, 1998

[54] SUPER ABSORBENT HYDROGEL FOAMS

[75] Inventors: Kinam Park; Haesun Park, both of West Lafayette, Ind.

[73] Assignee: Purdue Research Foundation, West Lafayette, Ind.

[21] Appl. No.: 416,269

[22] Filed: Apr. 4, 1995

[51] Int. Cl.$^6$ .......................... C08F 110/00; A61F 13/00
[52] U.S. Cl. .......................... 521/143; 528/392; 528/396; 424/426; 604/364; 604/342
[58] Field of Search .......................... 521/143; 528/392, 528/396; 424/426; 604/364, 372

[56] References Cited

U.S. PATENT DOCUMENTS

| | | | |
|---|---|---|---|
| 3,551,556 | 12/1970 | Kilmet et al. | 424/21 |
| 3,641,237 | 2/1972 | Gould et al. | 424/16 |
| 3,826,678 | 7/1974 | Hoffman et al. | 117/81 |
| 4,178,361 | 12/1979 | Cohen et al. | 424/22 |
| 4,801,457 | 1/1989 | Heller et al. | 424/422 |
| 5,147,343 | 9/1992 | Kellenberger | 604/368 |
| 5,149,335 | 9/1992 | Kellenberger et al. | 604/372 |
| 5,352,448 | 10/1994 | Bowersock et al. | 424/438 |

OTHER PUBLICATIONS

In vitro and in vivo studies of enzyme–digestible hydrogels for oral drug delivery. Waleed S.W. Shalaby et al. *Journal of Controlled Release*, vol. 19, pp. 131–144 (1992). The month of publication is not available.

Enzyme–digestible swelling hydrogels as platforms for long–term oral drug delivery: synthesis and characterization. K. Park. *Biomaterials*, vol. 9, Sep. 1988. The month of publication is not available.

Plastic Foams: the physics and chemistry of product performance and process technology. Calvin J. Benning. *Polymer Engineering and Technology*. vol. 1, Chapters 6,7,9,13,14 (1969). The month of publication is not available.

*Handbook of Polymeric Foams and Foam Technology*. Daniel Klempner and Kurt G. Frisch *Hanser Publishers*, Chapters 1–3, 12, 13, 16 and 17, 1991. The month of publication is not available.

*Principles of Polymer Systems*. Ferdinand Rodriguez. *Hemespher Publishing Corporation*, Second Edition, 1982. The month of publication is not available.

*Plastic Foams, Part II*. Kurt C. Frisch and James Sounders, *Marcel Dekker, Inc.* (1973). The month of publication is not available.

*Integral/Structural Polymer Foams: Technology, Properties and Applications*. G. Henrici–Olive et al. *Springer–Verlag*. (1986). The month of publication is not available.

Honey, I blew up the Hydrogels! Haesun Park et al. *Proceed. Intern. Symp. Control. Rel. Bioact. Mater.*, 21:21–22, Jun. 27–30, Nice, France, (1994). The month of publication is not available.

Hydrogel Foams: A New Type of Fast Swelling Hydrogels. Haesun Park et al. *The 20th Annual Meeting of the Society for Biomaterials*, Apr. 5–9, Boston, MA, USA, (1994). The month of publication is not available.

"Absorbent PVA Material Funds Medical Application" *Medical Product Manufacturing News Hotline*. Apr. 1, 1995.

*Primary Examiner*—P. Hampton-Hightower
*Attorney, Agent, or Firm*—Barnes & Thornburg

[57] ABSTRACT

A water swellable foam matrix formed as a macroporous solid comprising a foam stabilizing agent and a polymer or copolymer of a free radical polymerizable hydrophilic olefin monomer crosslinked with about 0.1 to about 10% by weight of a multiolefin-functional crosslinking agent is described. The foam matrix is characterized by rapid swelling and high water swelling ratios.

12 Claims, 3 Drawing Sheets

SUPER ABSORBENT HYDROGEL FOAMS

FIELD OF THE INVENTION

The present invention relates to a gas expanded polymer matrix and method for making the same. More particularly, this invention is directed to a polymer matrix characterized by rapid swelling and high water swelling ratios.

BACKGROUND AND SUMMARY OF THE INVENTION

Investigators have been searching for synthetic materials that are capable of absorbing aqueous solutions. One such material is the synthetic hydrogel matrices which comprise water insoluble, but water swellable crosslinked hydrophilic polymers. Suitable hydrophilic monomers for synthesizing hydrogels are known to those skilled in the art and include the hydrophilic monomers/polymers described in U.S. Pat. Nos. 4,178,361 and 3,551,556, the disclosures of which are expressly incorporated herein by reference.

One of the useful properties of hydrogels is their ability to absorb water and swell without dissolution of the matrix. As the hydrogel swells, the pore size of the hydrogel increases which enhances uptake of aqueous solutions and the diffusion of compounds out of the hydrogel. These properties have allowed use of hydrogels as controlled drug release systems and as absorbent materials. However, the rate of swelling of dried hydrogels upon exposure to an aqueous solution is limited by diffusion of water into the glassy polymer matrix. Conventional dried hydrogels have relatively small pore sizes resulting in slow swelling and release or absorption of liquids. Several applications, including their use as super absorbents and oral drug delivery vehicles, require a more rapid absorption of liquids than can be achieved using conventional hydrogels. Thus a polymer matrix that is capable of rapid swelling characteristics upon contact with water is highly desirable.

The present invention is directed to a composition and a method of preparing hydrogel foams. Hydrogel foams are polymer matrices formed by introducing a gas into a solution of hydrogel monomers during the polymerization of the monomers. Many of the same techniques used in the art to product art-recognized foams are useful for preparation of the present polymer foams. The present hydrogel foams have numerous gas cells, the majority of which are connected to form open channel systems. The size and number of the gas cells is determined by monomer concentration, the viscosity of the monomer solution, the extent of crosslinking, the presence/type of surfactant and the type and amount of gas introduced into the polymerizing solution.

Polymeric foams have been previously produced from materials such as polyurethanes, rubber, and poly(vinyl chloride). The key ingredient in the foaming process is a blowing agent (or foaming agent) which is defined as any substance or combination of substances capable of producing cellular structure within a polymer matrix.

Foaming agents are classified as physical and chemical foaming agents. Nitrogen and carbon dioxide are physical foaming agents that expand when pressure is released, resulting in the formation of a cellular structure in the polymer. Chemical foaming agents include compounds that react or decompose to form a gas upon exposure to reagents or environmental conditions. Chemical foaming agents are preferred over physical foaming agents due to the difficulty of obtaining a homogeneous blend and controlling the high gas pressure and diffusion rate of gas when utilizing physical foaming agents.

Polyurethane foams, or cellular polyurethanes, are manufactured by using blowing agents to form gas bubbles in the polymerizing reaction mixture. A silicone based surfactant is added to the reaction mixture to regulate the cell size, uniformity, and to control the viscosity and surface tension of the cell membranes. Polymerization is usually fast and exothermic and the heat generated vaporizes the liquid blowing agent. One blowing agent utilized is water which produces $CO_2$ gas from reaction with isocyanate. Additional blowing agents utilized to form polyurethane foams include low boiling point liquids that volatilizes during the reaction, such as fluorocarbon.

Foamed rubber is produced by different foaming process than polyurethane. Natural rubber latex is combined with a solution of soap, antioxidants, cross-linking agents, and foam stabilizers. The soap component produces a froth upon beating the mixture. Foaming is done by automatic mixing and foaming machines, known to those skilled in the art, that combine agitation and aeration during crosslinking process (curing or vulcanization). To produce an article, the foam is poured into the metallic mold and then heated to complete the crosslinking. In molding method, a system is mixed at a lower temperature than the decomposition temperature of the blowing agent. Upon heating to 150°–200° C. in a mold, gas generation and gelation occurs at the same time. In an open and extrusion method, a plastisol containing a blowing agent is spread on a substrate and fused without a second confining surface. Mechanical foaming method is also used. A substantial amount of $CO_2$ can be dissolved in the plasticizer phase when mixed at about 7 atm and below room temperature. Release of pressure through a nozzle yields a stream of foamed, unfused plastisol.

Some thermoplastics such as polyethylene, polypropylene and cellulose derivatives can also be foamed by blowing agents. The blowing agent can be selected based on the consideration of the decomposition temperature, the volume of the gas generated per unit weight and the nature of the decomposed residues.

In general, polymeric foams are produced by expanding or vaporizing the dissolved blowing agent during or after polymerization. These foaming techniques have been used in the present invention to produce a hydrogel foam.

The present invention is directed to the formation of hydrogel foams that have a rapid swelling response, wherein the hydrogel foam exhibits a water swelling ratio of at least 15 within one hour of contact with an aqueous solution. The hydrogel foams of the present invention are also capable of swelling to at least fifteen times the original weight of the dried matrix. The hydrogel foams of the present invention can be used as platforms for once-a-day oral drug delivery systems, biodegradable swelling products for diet control, fast absorption of blood during surgery, super swelling materials for personal hygiene products, or as materials for purifying biotechnology products such as peptides and proteins (i.e. use as filters or chromatography materials).

BRIEF DESCRIPTION OF THE DRAWINGS

FIG. 2 is a graphic representation comparing the swelling kinetics of polyacrylamide (PAM) hydrogels (the control)

and PAM hydrogel foams prepared using different concentrations of bovine serum albumin.

DETAILED DESCRIPTION OF THE INVENTION

The hydrogel foams produced in accordance with the present invention have properties that make them uniquely adapted for use as superabsorbent materials. One unique property of hydrogel foams is their ability to swell extremely fast in aqueous solution. When the dried hydrogel foam of the present invention (having an open cell structure) is placed in an aqueous solution, water flows through the open channels by capillary effect, and rapidly swells the hydrogels. Conventional hydrogels also swell upon contact with an aqueous solution, but the swelling rate is much slower. For example, when hydrogels and hydrogel foams are formed in the size of conventional tablets (having a size range of 5–10 mm in diameter) and are contacted with water, hydrogel foams will complete swelling in less than an hour, while the hydrogels take more than 12 hours to reach an equilibrium swelling.

Hydrogel foams also swell to a much larger extent than the conventional hydrogels made of the same materials at the same concentration. Hydrogel foams in accordance with this invention can absorb more than 100 times its own weight of aqueous solution. In one embodiment in accordance with the present invention, a hydrogel foam is formed wherein the ratio of the volume of the gas phase to the volume of the solid phase is at least one. In another embodiment, a volume of the hydrogel foam of this invention having a size greater than 1 mm in its smallest dimension exhibits a water swelling ratio of at least 15 within one hour of contact with an aqueous solution. In a further embodiment, a volume of the hydrogel foam of this invention having a size greater than 1 mm in its smallest dimension exhibits at least 50% of its maximum swelling ratio within one hour of contact with an aqueous solution.

The hydrogel foams of the present invention are prepared by introducing a gas into an monomer solution comprising at least one hydrophilic olefin monomer compound, about 0.1 to about 10% by weight of a multiolefin-functional crosslinking agent and a surfactant, during polymerization of the olefin monomer. Preferably the polymerization reaction is conducted in an aqueous solution; however non-aqueous solvents, preferably water miscible non-aqueous solvents such as alcohols, ethers, dimethyl sulfide, dimethyl formamide and the like, can also be used to form the hydrogel foams in accordance with the present invention.

Hydrophilic olefin monomers for use in accordance with the present invention include those monomers having hydroxyl, keto and amino functionalities in addition to the alkene functionality. Suitable hydrophilic monomers for synthesizing hydrogels are known to those skilled in the art and include the hydrophilic monomers/polymers described in U.S. Pat. Nos. 4,178,361 and 3,551,556 the disclosure of which is expressly incorporated herein by reference. In particular, hydrogel foams of poly(acrylic acid) (PAA), polyacrylamide (PAM), polyvinylpyrrolidone (PVP), poly (2-hydroxyethyl methacrylate) (PHEMA), and poly(2-hydroxypropyl methacrylate) (PHPMA) have been prepared.

It is also anticipated that the hydrogel foams of the present invention can be formed from solutions of several different monomer species to form a co-polymer based hydrogel foam. The concentration of the monomer ranges from 5% to 80% depending on the type of the monomer. The minimum concentration of monomer in aqueous reaction mixtures required to form a foam structure that maintains its structural integrity has been determined for the following monomers:

| | |
|---|---|
| Acrylamide | 5% |
| Acrylic Acid | 8% |
| Vinylpyrrolidone | 15% |
| 2-Hydroxyethyl methacrylate | 40% |
| 2-Hydroxypropyl methacrylate | 80% |

Polymerization of the olefin monomers is initiated by a free radical mediated reaction. Free radical initiators are well known in the art and the nature of such is not typically critical to the polymerization reaction. Ammonium persulfate (APS) and N, N, N', N'-tetramethylethyldiamine (TEMED) have been used as the initiators for PAM, PAA, PHPMA and PHEMA hydrogels, while 2, 2'-azobis (2-amidinopropane) dihydrochloride (Wako Pure Chemicals), a water soluble azo-initiator has been used for PVP and gels.

The olefin monomers are polymerized in the presence of a multiolefin-functional crosslinking agent. Typically the crosslinking agent concentration ranges from about 0.1 to about 10%, more typically about 0.1 to about 1.5% by weight relative to the olefin monomer. A multiolefin-functional crosslinking agent is defined herein to include any compound having at least two alkenyl groups. One multiolefin-functional crosslinking agent used in accordance with the present invention is N, N'-methylene-bis-acrylamide (BIS). Other suitable bifunctional olefin crosslinking agents include diallyl phthalate, diallyl isophtholate, diallyl benzene and divinyl pyridine. The crosslinking agent can also be a biodegradable protein or carbohydrate that has been functionalized by covalent coupling with compounds bearing pendent alkenyl groups.

Alkenyl (—CH=CH$_2$) groups can be introduced to proteins using various agents including acrolein and glycidyl esters such as glycidyl acrylate or glycidyl methacrylate. Acrolein or glycidyl acrylate reacts with amine groups of the protein and introduces vinyl groups on the protein. The vinyl groups on the protein can participate in the polymerization of vinyl monomers such as acrylic acid, acrylamide, etc. Since each protein molecule presents more than one vinyl group which can participate in the polymerization, the functionalized protein molecules serve as effective crosslinking agents. The amount of vinyl groups introduced into albumin molecules can be varied by changing the amount of the modifying agents and the reaction time. An additional advantage to using a functionalized protein as the crosslinking agent arises from the biodegradability of proteins. Thus a hydrogel foam can be prepared that is bioerodible and will disintegrate upon exposure to enzymatic digestion.

The structure of hydrogel foams depends on the relative kinetics of polymerization and foaming. Gas bubbles must be produced after gelation starts but before all the crosslinks are formed so that they can be captured inside the gel. The duration of gas production, however, is generally very short compared to polymerization process and this can result in foam collapse, particularly when the surface tension of the solution is high, as in the case of acrylamide or acrylic acid where more than 70% of the monomer solution is water. The inclusion of a surfactant in the polymerization solution helps to alleviate this problem.

The term "surfactant" as used herein is defined as any composition that when dissolved in a liquid, reduces the surface tension of the liquid to the extent that a gas can be introduced into the liquid solution of the surfactant to form a foam. Surfactants for use with the present invention include proteinaceous surfactants, such as gelatin, albumin, ovalbumin, as well as nonproteinaceous surfactants including commercially available anionic, cationic and nonionic surfactants and known foam stabilizers, such as Pluronics, FPAN, Triton X, linoleic acid and SDS.

The hydrogel foams of the present invention are formed by introducing gas into a hydrophilic olefin monomer solution during polymerization of the monomer. The gas can be introduced into the polymerizing matrix by mechanical means or through the use of a blowing agent (or foaming agent). Mechanical means includes the use of a high speed blender or propeller or the introduction of gas into the liquid through a capillary or microporous surface. A blowing agent is defined herein as any substance or combination of substances capable of producing a gas upon exposure to environmental or chemical reagents. Examples of blowing agents are carbonates or metal powders which react with acidic condensation catalysts to generate $CO_2$ or $H_2$ and chemical agents that liberate expanding gas under the influence of heat, such as dipotassium-diazomethionate, N-nitroso-$\beta$-amino ketones and sodium borohydride. Combinations of various blowing agents or combinations of blowing agents with mechanical means can also be used to introduce gas into the hydrophilic olefin monomer solution during polymerization of the monomer.

To produce uniform air cells in the formed foams, the blowing agent must be uniformly dispersed or dissolved rapidly and decomposed smoothly in conjunction with the attainment of a high viscosity or gelation of the polymer system. If gelation occurs before gas release, fissures or holes are formed in the foam matrix. Gas cells formed too soon before gelation result in separation of the polymer into foam and gel phases. This produces a course, unevenly formed hydrogel foam.

In one embodiment of the present invention, sodium bicarbonate is used as the blowing agent. Sodium bicarbonate is completely soluble in water, nonhygroscopic, inexpensive, abundant, and available commercially in several particle size grades ranging from a fine powder to a free-flowing uniform granule. It is ingestible and is, in fact widely used as an antacid either alone or as a part of antacid products.

Sodium bicarbonate is easy to introduce to the solution before gelation and can yield approximately 52% carbon dioxide. The gas liberated ($CO_2$) and the products of its decomposition are noncorrosive, nontoxic, and nonflammable. The compound and the gas liberated are readily dispersed or dissolved in the monomer and polymer solution.

Polymerization at room temperature using TEMED and APS is pH-dependent. The addition of TEMED raises the pH of the monomer mixture and this increases the rate of polymerization. However, increasing the pH decreases $NaHCO_3$ effectiveness as a blowing agent, yet reducing the pH to a neutral or acidic level inhibits the initiation of polymerization significantly. Therefore, acidity, amount of TEMED and APS should be balanced to obtain sufficiently good foaming efficiency and reasonably fast polymerization kinetics as well. In one embodiment the polymerization reaction is conducted at a weakly acidic pH which results in slow initiation.

During the foaming process, the temperature of the mixture rises due to the heat of polymerization. Temperatures over 65° C. resulted in heat decomposition of the blowing agent and expansion of each cell. This leads to the great increase of the volume of hydrogel foams. As the temperature of the system returns to room temperature after polymerization was complete, the expanded hydrogel foams tend to collapse. Hydrogel foams prepared in this manner often result in closed cell structure. When the temperature was kept under 60° C. during foaming the polymerization, gas generation was mainly by the acid decomposition of the carbonates. Hydrogel foams made this way have a greater proportion of open cell structures.

Heat decomposition of the blowing agent can be minimized through the use of a combination of redox initiators, such as persulfate and N, N, N', N'-tetramethylethyldiamine (TEMED), and initiating the polymerization process at room temperature. A larger amount of acid is required to keep the mixture acidic when TEMED was used since TEMED is alkaline.

Temperature can also greatly affect the kinetics of polymerization. To ensure consistent polymerization kinetics the temperature of the polymerization reaction was held within a ±1° C. fluctuation range. A consistent rate of polymerization is desirable to optimize the time for $NaHCO_3$ addition and produce a reproducible hydrogel foam matrix having the desired characteristics. The foam must be stabilized for a critical time period until the polymerization reaction increases the molecular weight of the polymer to a point where the polymer is insoluble and the foam is self-supporting.

In one embodiment the hydrogel foam includes one or more functional particulate fillers. Appropriate fillers for use in accordance with the present invention include materials that increase the strength of the foam or highly absorbent materials, such as activated charcoal or other carbon materials that augment the absorption characteristics of the foam. Preferably the added fillers are evenly dispersed throughout the monomer solution during the polymerization reaction. This can be accomplished through the use of mixing, for example the use of a high speed mixer or blender. The concentration of the added filler is limited to levels which do not interfere with foam functionality.

In one embodiment about 1% (by weight) of carbon particles was added to the monomer solution to form a hydrogel foam. It is anticipated that carbon particles can be added up to a concentration of about 10% without effecting the formation of the foam.

In one embodiment the hydrogel foam is prepared from a water based monomer solution. After complete formation of the hydrogel foam, the foam is contacted with (typically immersed in) a volatile water misible solvent, such as methanol, ethanol or acetone. The hydrogel foam can be sequentially immersed in a series of solvents to replace the water from the original polymerization medium with the volatile water misicible solvent. It has been found that upon drying of the solvent exchanged matrix, the resulting foam shinks to a lesser extent than it does without the water/solvent exchange.

After formation of the hydrogel foam, the foams are dried to remove solvent from the foam matrix. Typically the hydrogel foam is blotted with absorbant materials to remove bulk quantities of water and air dried at room temperature. Alternatively, dry air can be drawn across the foam to increase the rate of drying, and optionally the foam can be heated during the drying process. The foam is dried until there is little or no additional loss of weight upon further drying. Typically the foam is dried at room temperature for 10–36 hours. In one embodiment the foam is placed in a "food dehydrator" (commercially available) wherein a fan blows warm air across the surface of the foam. Using such a device, drying of the foam is complete after 10–14 hours.

The properties of the formed hydrogel foams can be altered by changing the following parameters: 1. the concentration of the blowing agent; 2. the acidity of the solution; 3. the temperature; 4. the viscosity of the medium; 5. the concentration of the foam stabilizer; and 6. the pressure applied during foam formation.

Generally, hydrogel foams are formed having both open and closed cell structures. The proportion of closed-cell structures to open cell structures can be modified by altering the concentration of the monomer and crosslinking agents or by controlling the polymerization conditions. For example the number of closed structures is increased when the foam is produced under pressure (i.e. greater than atmospheric pressure) or at temperatures greater than 65° C., whereas the percentage of open cell-foams are increased when the foam is formed at temperatures below 65° C. and at atmospheric pressure or less than atmospheric pressure. The cell structure of the foam is important because it determines the swelling kinetics of the hydrogel foam. The swelling of a hydrogel foam having closed cell structures is substantially slower than hydrogel foams having open cell structures.

The density of hydrogel foams depends on monomer concentration, the functionality and concentration of the crosslinking agent, the amount of gas introduced into the polymerizing mixture as well as other components used in the synthesis. The density of hydrogel foams prepared in accordance with the present invention range from about 0.015 to about 0.7 and more preferably range between 0.015 to 0.5. If the density of the hydrogel foam is too low (lower than 0.015), then the foam does not maintain sufficient structural integrity for practical applications. If the density is too high (greater than 0.5), the hydrogel foams may not swell fast enough.

By varying the polymerization conditions and components gels and gel foams were prepared having the following densities:

|  | Hydrogel | Foam (water*) | Foam (ethanol**) |
| --- | --- | --- | --- |
| PAA: | 1.05–1.30 | 0.15–0.40 | 0.015–0.04 |
| PAM: | 1.30–1.50 | 0.15–0.30 | 0.015–0.03 |
| PVP: | 1.20–1.40 | 0.15–0.50 | 0.015–0.05 |
| PHEMA: | 1.40 | 0.15–0.40 | 0.015–0.04 |
| PHPMA: | 1.40 | 0.15–0.35 | 0.015–0.04 |

*Hydrogel foams containing water were dried.
**Hydrogels were placed in ethanol to replace water before drying.

The hydrogel foams of the present invention can be formed into a variety of shapes and sizes depending on the quantity of the monomer and the shape of the vessel containing the monomer mixture. The hydrogel foams can be poured into molds and allowed to cure so that the formed foam conforms to the shape of the mold. Alternatively the foam can be formed as a large block which can subsequently be fractured or ground into smaller pieces or particles.

Experiments data as well as theoretical calculations based on the diffusion coefficient of water through hydrogels (assuming $D=10^{-6}$ cm$^2$/sec) indicate that hydrogel foams will have enhanced swelling kinetics over conventional hydrogels when the hydrogel has a size larger than 1–3 mm in its smallest dimension. The hydrogel foams of the present invention swell to at least 50% of the equilibrium swelling ratio in less than one hour after contact with water.

EXAMPLE 1
Functionalization of Albumin

A 5% human albumin (Sigma, Fraction V) solution was prepared using a 1/2X phosphate buffered saline (PBS) solution. To 10 ml of this solution, 200 µl of glycidyl acrylate (Aldrich) was directly added while stirring. After 6 hr, 1 ml of 20% glycine solution was added and stirring was continued for another 30 min. This protein solution was then dialyzed against 2 liters of 1/2X PBS. During 24 hr of dialysis the buffer was changed 5 times. After the protein was collected, the concentration was adjusted to make 3% albumin solution. The degree of alkylation was determined by measuring the free amine groups of albumin. The functionalized albumin had a cross-linking function, so that a gel was formed when they are copolymerized with other monomers. The functionalized albumin was used to synthesize biodegradable hydrogels and hydrogel foams.

EXAMPLE 2
Synthesis of Poly(acrylic Acid) Foams

Poly(acrylic acid) foams have been prepared using either N, N'-methylene-bis-acrylamide (BIS) or functionalized albumin as a crosslinking agent. In polyacrylic acid foams crosslinked with BIS, the BIS was dissolved in acrylic acid (AA) to make a final concentration of 1% (w/v) BIS (i.e., 150 mg of BIS was dissolved in 15 ml of AA). All the components were then mixed in a glass test tube (15×85 mm) containing deionized distilled water (DDW) as described in Table 1.

TABLE 1

Amounts of each components added to make poly(acrylic acid) hydrogel foams.

|  | Foam 1 | Foam 2 | Foam 3 |
| --- | --- | --- | --- |
| AA/BIS mixture | 0.2 ml | 0.3 ml | 0.4 ml |
| DDW | 0.6 ml | 0.5 ml | 0.3 ml |
| TEMED (10%) | 50 µl | 50 µl | 50 µl |
| NaHCO$_3$ | 0.1 ml | 0.1 ml | 0.2 ml |
| APS (10%) | 50 µl | 50 µl | 50 µl |

Ammonium persulfate (APS) was added last. After the addition of APS, the tube was immediately immersed in a 60° C. water bath about 15 sec. After the test tube was removed from the water bath, a NaHCO$_3$ suspension (70% w/v) was added dropwise every 5–10 sec with constant shaking by hand. In the beginning, foaming was vigorous due to the strong acidic pH. Addition of NaHCO$_3$ raised the pH of the solution towards a neutral pH which is more favorable for redox initiation. As the amount of the added NaHCO$_3$ increased (about 2–3 drops) the pH of the mixture became high enough for the initiators to start the polymerization reaction. The optimum pH for TEMED-APS initiators is between 8 and 9. However such a high pH is not desirable, since acidic pH is necessary for the decomposition of NaHCO$_3$.

Figure 1:
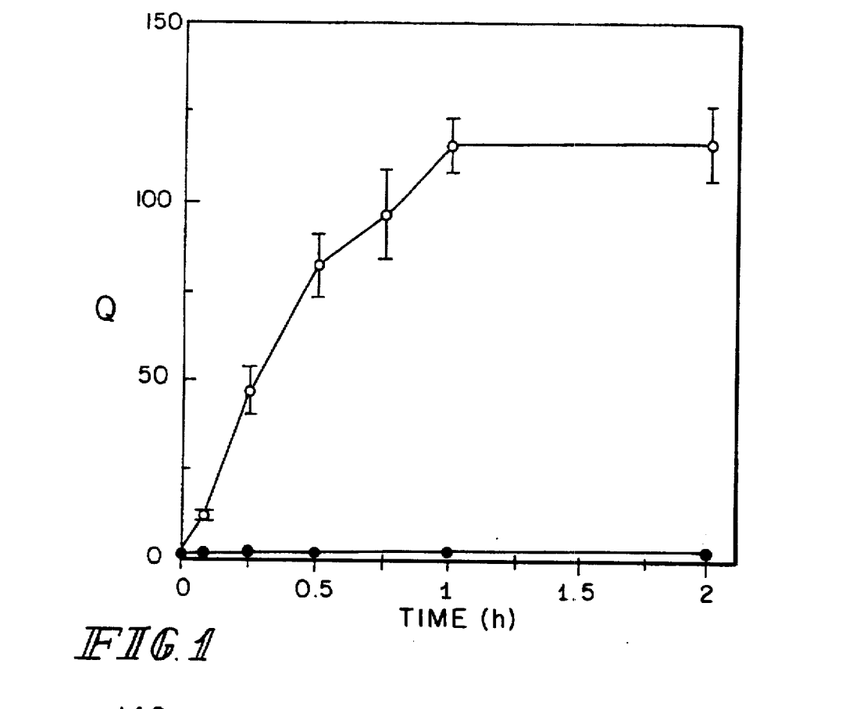
FIG. 1 is a graphic representation comparing the swelling kinetics of poly(acrylic acid) (PAA) hydrogels (solid circles) and PAA hydrogel foams (open circles) which were each synthesized using the same concentration of the AA monomers. The weight of the hydrating samples were measured at timed intervals, and the swelling ratio (Q) was calculated as the ratio of weights of the hydrated and dried gels.

FIG. 1 compares the swelling kinetics of PAA hydrogels (represented by solid circles) and PAA hydrogel foams (represented by open circles) which were each synthesized using the same concentration of the AA monomers. The weight of the hydrating samples were measured at timed intervals, and the swelling ratio (Q) was calculated as the ratio of weights of the hydrated and dried gels. It is apparent that the PAA hydrogel foams swell to reach an equilibrium after 1 h of swelling, while the PAA hydrogels did not swell during the same period of time.

PAA is partially neutralized by $NaHCO_3$ during foaming. This built-in neutralization effect results in extremely fast swelling of the PAA hydrogel foams even in the absence of the surfactant albumin during synthesis of the foam (FIG. 1). The swelling ratio during the first 5 min of hydration was larger than 10. The PAA hydrogel foam reached 70% of the equilibrium swelling within 30 min, while conventional PAA hydrogel took more than 3 days to reach 70% of the equilibrium swelling.

EXAMPLE 3

Synthesis of Polyacrylamide Hydrogel Foams

Acrylamide was dissolved in DDW to make an acrylamide solution having a final concentration of 50% (W/V) acrylamide. BIS was dissolved in the acrylamide solution to a final concentration 1% of the monomer. TEMED, ammonium persulfate and $NaHCO_3$ and bovine serum albumin (BSA) were added in accordance with Table 2. The final pH of the solution was between 4.5 and 5.0. APS was added last and the time for the initiation of the polymerization was measured.

TABLE 2

Amounts of each components added to make polyacrylamide hydrogel foams.

| | |
|---|---|
| 50% Acrylamide (with 1% BIS) | 600 μl |
| Acrylic acid or HCl | 25 μl |
| 10% TEMED | 40 μl |
| 10% Ammonium persulfate | 40 μl |
| $NaHCO_3$ | 18 μl |
| 0.5% Bovine serum albumin (BSA) | 0 μl with 295 μl of water (for 0%*) |
| | 20 μl with 275 μl of water (for 0.01%*) |
| | 50 μl with 245 μl of water (for 0.025%*) |
| | 100 μl with 195 μl of water (for 0.05%*) |
| | 200 μl with 95 μl of water (for 0.1%*) |

*The final concentration of BSA in the mixture.

The time for the gelation was determined by testing the viscosity change of the solution. The viscosity change was examined by withdrawing a small amount of the solution using a pipet. When the gelation started, the solution could not readily be drawn up into the pipette. Monomer mixtures which were polymerized without a foaming agent were used as control gels. To make hydrogel foams, $NaHCO_3$ was added to the tube containing monomer solution at the predetermined time point (as determined by monitoring the change in viscosity determined as described above) and stirred gently with a small spatula to distribute and dissolve $NaHCO_3$ particles. Usually foaming was instantaneous upon the addition of $NaHCO_3$.

Figure 2:
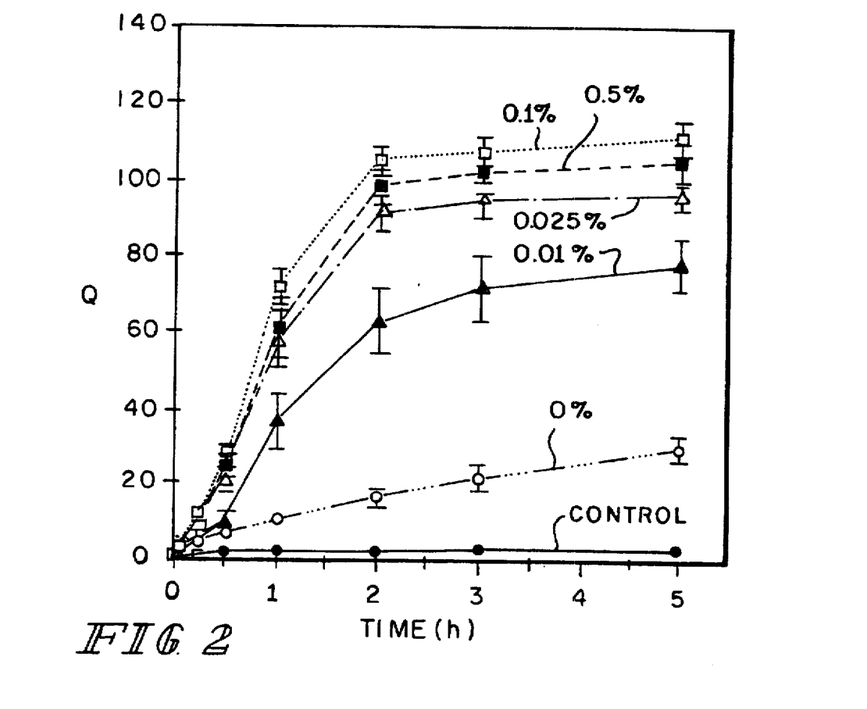

The addition of $NaHCO_3$ raised the pH of the mixture slightly. This accelerated the polymerization process. During foaming, polymerization proceeded and the foamed mixture became viscous. Stirring was stopped as the mixture lost fluidity. The test tube was placed back in the test tube holder without any further disturbances until polymerization was completed. The effect of the surfactant, BSA, on the swelling kinetics of PAM hydrogel foams is shown in FIG. 2. The data shows that increased concentrations of BSA in the hydrogel foams further increases the swelling ratio of the hydrogel foams compared to the conventional hydrogels.

EXAMPLE 4

The Effect of $NaHCO_3$ on the Swelling of the Hydrogel Foams

Figure 3:
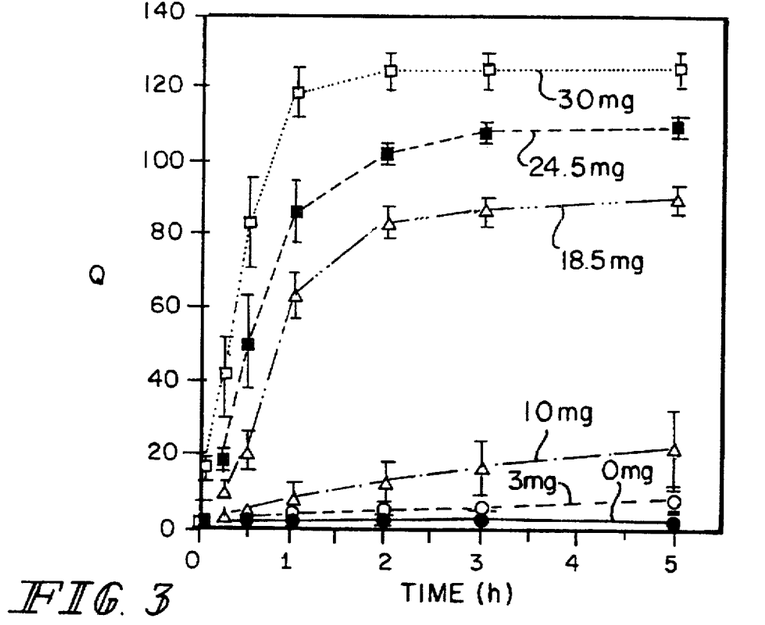
FIG. 3 is a graphic representation comparing the swelling kinetics of polyacrylamide (PAM) hydrogel foams prepared using different concentrations of NaHCO$_3$.

The amount of the $NaHCO_3$ added was varied to determine its effect on the swelling of the hydrogel foams. The amount of $NaHCO_3$ was varied from a 1 mg to 30 mg for 1 ml of the acrylamide monomer mixture as shown in Table 3. FIG. 3 shows that as the amount of $NaHCO_3$ was increased, the swelling ratio of the hydrogel foams increased. This indicates that the amount of $NaHCO_3$ added for the foam formation is important in the swelling kinetics and the equilibrium swelling ratio.

TABLE 3

The volume of the hydrogel foams as a function of the amount of the added $NaHCO_3$.

| $NaHCO_3$ (mg) | Gel Volume (%) |
|---|---|
| 0 | 100 |
| 3 | 100 |
| 10 | 155 ± 69 |
| 18.5 | 356 ± 35 |
| 24.5 | 503 ± 32 |
| 30 | 570 ± 70 |

EXAMPLE 5

Synthesis of Polyvinylpyrrolidone Hydrogel Foams 500 mgs of BIS was dissolved in 50 ml of vinylpyrrolidone (VP) to make the final concentration of 1% BIS. The components listed in Table 4 were mixed in a glass test tube (15×85 mm) and placed in a 60° C. water bath immediately after the initiator, 2, 2'-azobis (2-amidinopropane) dihydrochloride (V-50), was added. The test tubes were kept at 60° C. for 45-75 sec before adding $NaHCO_3$. Gelation time of the polymerization reaction was determined as described in Example 2.

To form the hydrogel foams, the test tube was taken out of the 60° C. water bath immediately before gelation and $NaHCO_3$ was added. Upon addition of $NaHCO_3$, the gel started bubbling vigorously.

Acidity is required to foam the polymerizing VP solution. In the absence of added HCl or acrylic acid (AA), VP alone polymerized in 2 min. Addition of HCl inhibits the polymerization of the system and the gel was not formed. However a small amount of AA increases polymerization, and a gel was formed in 1 min at 60° C. with the addition of 20 μl of AA.

TABLE 4

Amounts of each components added to make polyvinylpyrrolidone hydrogel foams.

| | Foam 1 | Foam 2 | Foam 3 |
|---|---|---|---|
| VP/BIS | 0.3 ml | 0.4 ml | 0.5 ml |
| DDW | 0.5 ml | 0.4 ml | 0.3 ml |
| AA | 20 μl | 20 μl | 20 μl |
| 10% V-50 | 75 μl | 75 μl | 75 μl |
| $NaHCO_3$ | 105 μl | 105 μl | 105 μl |

EXAMPLE 6
Synthesis of PHEMA Hydrogel Foams

Figure 4:
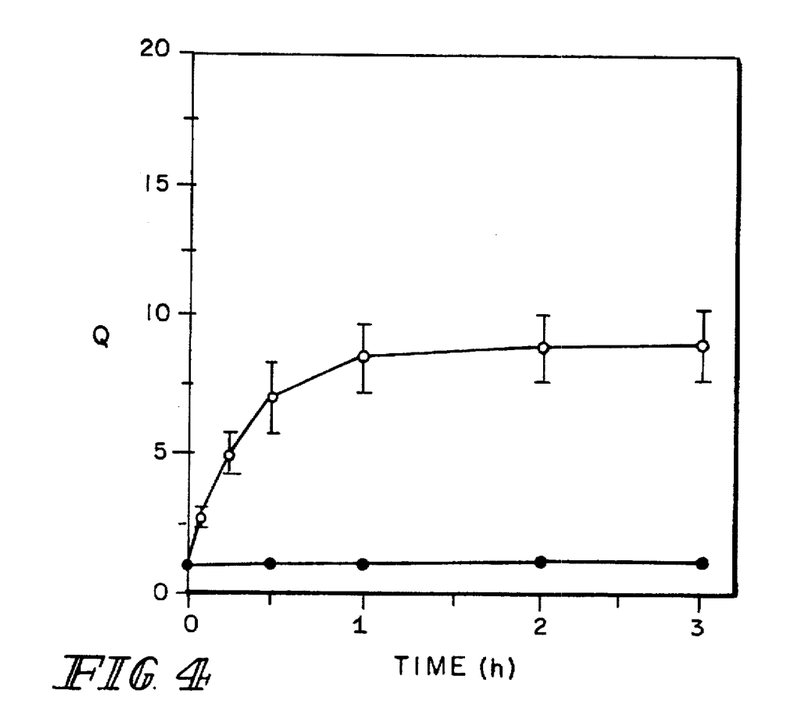
FIG. 4 is a graphic representation comparing the swelling kinetics of poly(2-hydroxyethyl methacrylate) (PHEMA) hydrogel foams (open circles) compared to the PHEMA hydrogels (solid circles).

BIS was dissolved in 2-hydroxyethyl methacrylate (HEMA) to make the final BIS concentration of 1% (w/v) of the monomer. The components used to make PHEMA hydrogels and hydrogel foams are listed in Table 5. The monomers polymerized between 10–15 minutes after addition of APS to the mixture. To determine when polymerization began, a closed-ended pipet was used to check the mixture. When "strings" from the gel appeared at the end of the pipet tip as the tip was lifted from the mixture, it was considered right timing for $NaHCO_3$ addition. A $NaHCO_3$ suspension was made by adding 3 g of $NaHCO_3$ in 2 ml of water. $NaHCO_3$ (20 mg in 15 μl of suspension) was added and stirred vigorously with a small spatula (this process is known as "beating") and then left undisturbed. Numerous tiny bubbles were formed during the beating. As polymerization progressed, more bubbles were formed and the volume of the gel increased due to the bubble growth in size and number. The maximum gel volume was reached after an additional 8–10 minutes at which point polymerization and crosslinking no longer allowed free expansion of the foam gel. FIG. 4 shows the fast swelling kinetics of the PHEMA hydrogel foams (represented by open circles) compared to the PHEMA hydrogels (represented by solid circles). The swelling of PHEMA hydrogel was almost negligible while the swelling ratio of the PHEMA hydrogel foams reached close to 10 after contacting water for one hour.

TABLE 5

Amounts of each components added to make PHEMA hydrogel foams.

|  | PHEMA | PHEMA-Foam |
| --- | --- | --- |
| HEMA/BIS sol'n | 800 μl | 800 μl |
| Acrylic acid | — | 40 μl |
| DDW | 40 μl | 0 μl |
| 10% TEMED | 80 μl | 80 μl |
| 10% APS | 80 μl | 80 μl |
| $NaHCO_3$ | — | 20 mg |

EXAMPLE 7
Synthesis of PHPMA Hydrogel Foams 100 mg of BIS was dissolved in 2-hydroxypropylmethylacrylate (HPMA) to make the final volume of 10 ml [concentration of BIS was 1% (w/v) of the monomer]. The monomer mixture was prepared by adding the compounds as follows: HPMA-BIS (0.8 ml); acrylic acid (40 or 45 μl); 10% TEMED (80 μl). The monomer mixture (total of 1 ml) was placed in a glass tube (15×85 mm). The concentration of HPMA should be higher than 80% to form a HPMA hydrogel foam. The optimum pH for the foaming of HPMA is near 5.0. The mixture became cloudy with the addition of APS. The tube was gently shaken and left in the tube holder without any further disturbances. Gelation usually started in 6 to 8 min depending on the presence of external disturbances. The more the disturbance of the mixture during the polymerization period, the slower the gelation.

The onset of gelation was determined as described in Example 5. Several drops of $NaHCO_3$ suspension (about 30 mg) were added and thoroughly mixed with a small spatula until tiny bubbles were generated inside the entire gel. Usually $NaHCO_3$ was added 8 or 9 min after the addition of APS. Excessive beating was not desirable since it results in premature foaming before completion of the gelation. The test tube is left in the tube holder after mixing the $NaHCO_3$ without further disturbances. Initially, the foam generated during beating subsides, but 12–15 minutes after the addition of APS, the volume of the gel starts to rise again due to the increase in the number and the size of bubbles.

Initial gas forming was mainly due to the acid decomposition of $NaHCO_3$. However, additional decomposition of $NaHCO_3$ was induced by the heat generated during polymerization. Generation and expansion of gas bubbles responsible for foam rise during polymerization appears to be due to the heat decomposition of $NaHCO_3$. This was tested with and without acid in the monomer mixture. Without acid in the feed mixture, initial bubbling followed by $NaHCO_3$ addition was absent. However, after polymerization started, some bubbles appeared in the gel and the volume of the gel expanded. Nevertheless, the final volume of the foam gel was far smaller than the gel formed in the acidic condition. Without heat, a similar result was obtained. When gelation started, the tube was immersed in a cold water bath (20° C.) to dissipate the heat from polymerization. In this case, not only active foaming did not occur, but also polymerization was retarded.

Figure 5:
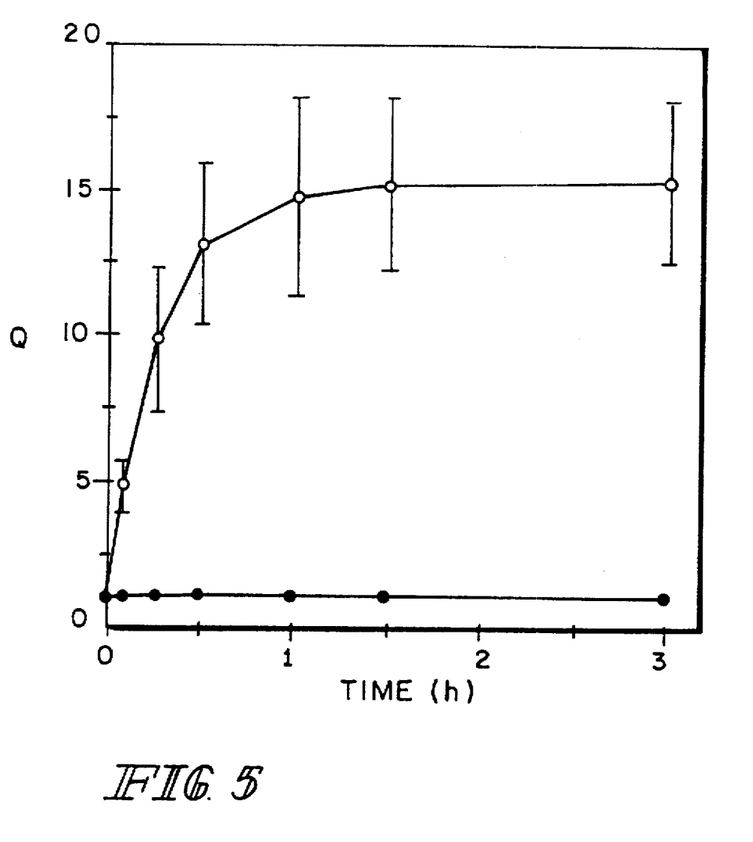
FIG. 5 is a graphic representation comparing the swelling kinetics of poly(2-hydroxypropyl methacrylate) (PHPMA) hydrogel foams (open circles) compared to the PHPMA hydrogels (solid circles).

As the polymerization progressed, the volume of the foam increased until polymerized network no longer allowed expansion of the gel. Foam rise reached the maximum usually in 10 minutes. The tube was kept in 60° C. water bath for further stabilization. FIG. 5 compares the swelling of the PHPMA hydrogel foams (represented by open circles) to the swelling of PHPMA hydrogels (represented by solid circles). The swelling of the hydrogels was negligible while the hydrogel foams absorbed the aqueous solution more than 15 times the dried hydrogel foams.

EXAMPLE 8
Comparison of Foam Stabilizers

The foam stabilizing effects of gelatin (calf skin), egg white protein and bovine serum albumin were compared. A series of protein solutions with concentrations ranging from 0.005% to 4% were prepared. 0.45 ml of each solution was placed in a glass test tube (13×100 mm) and 30 μl of acrylic acid (or citric acid) was added. The pH of the solution at this point was near 3.0. 20 mg of $NaHCO_3$ (20 μl of $NaHCO_3$ suspension) was then added and the tube as gently shaken by hand for a few seconds to aid dispersion and dissolution of the $NaHCO_3$ particles. Foam started to rise immediately upon the addition of $NaHCO_3$. Foam raised to the transient maximum height in several seconds and then gradually subsided. Column height of the foam at the maximum rise was recorded. To compare the foam stabilizing effect of each protein solution, the column height of the foam after 1 min was also recorded.

The overall foaming efficiency was dependent on the concentration of the stabilizer used, the amount of $NaHCO_3$ added, and the pH of the solution. The size of bubbles and maintenance of foams were directly related to the concentration of the surfactant used. Fine gas bubbles had large interfacial area for given foam volume compared to larger size gas bubbles and thus required more surfactant. Insufficient amount of surfactant resulted in combination of aggregated gas cells resulting from an attempt of the system to reduce the interfacial area. This led to gradual collapse of the foam.

It was observed that the generation of gas was maximum when the pH of the aqueous medium stayed near 5 during foaming. It should be noted that sodium bicarbonate is basic in aqueous solution. Thus, when it was added to the aqueous solution, pH of the aqueous solution shifted to the alkaline side. Therefore, the initial pH of the solution before the addition of $NaHCO_3$ should be sufficiently low that the pH of the solution after NaHCO$_3$ addition should not exceed 5. The original pH of the aqueous solution was maintained near 3, when 15–30 mg of NaHCO$_3$ was used per 1 ml of the monomer solution.

For some polymerization reactions, keeping pH near 3 may not be possible particularly when polymerization is initiated at room temperature. TEMED-APS initiators require the alkaline pH to initiate polymerization at room temperature. Therefore, a balance must be obtained that allows good polymerization kinetics as well as sufficient foaming. Each case must be studied to find the optimum condition to balance the polymerization kinetics and foaming. Acidity (amount of acid), amounts of TEMED and APS, and the need of external heat are the three major conditions that must be determined.

Table 6 shows the results of a study on the effects of protein surfactants on the formation of foams. The foaming efficiency and the foam stability were greatly improved by the addition of foam stabilizing agents such as albumin. FIG. 2 shows the effect of the albumin concentration added to the foaming solution. As the concentration of albumin increased to 0.025%, the swelling of the hydrogel foam increased significantly with the equilibrium swelling ratio close to 100. In the presence of 0.1% albumin, the volume of the PAM foam at the maximum rise was 3.5 times larger than that of the starting monomer solution, and the foam was sustained for several minutes in contrast to several seconds in the absence of albumin. The increase in the concentration of albumin to 0.2% resulted in even higher swelling ratio of the hydrogel foams. In all the hydrogel foams tested, the swelling ratio increased to more than 2 within the first five minutes. Hydration kinetics were directly related to the concentration of albumin in the monomer solution (FIG. 2).

TABLE 6

The height (in mm) of the foam column measured at the peak height and after 1 min of foaming after adding protein surfactants

| | Peak Height | Height after 1 Min. |
|---|---|---|
| No Protein | 26 ± 6 | 8 |
| Gelatin | | |
| 0.05 | 26 | 11 |
| 0.1 | 29 ± 5 | 16 ± 6 |
| 0.5 | 28 | 14 |
| 1.0 | 32 ± 6 | 25 ± 7 |
| 2.0 | 34 ± 1 | 30 |
| Egg White Protein | | |
| 0.02 | 38 | 24 |
| 0.05 | 35 ± 3 | 27 ± 10 |
| 0.1 | 39 ± 6 | 33 ± 8 |
| 0.2 | 39 | 39 |
| 0.5 | 38 ± 4 | 38 ± 4 |
| 1.0 | 45 | 45 |
| Bovine Serum Albumin | | |
| 0.005 | 44 ± 3 | 16 ± 8 |
| 0.01 | 46 ± 2 | 32 ± 1 |
| 0.02 | 45 ± 4 | 36 ± 4 |
| 0.05 | 46 ± 4 | 37 ± 1 |
| 0.1 | 45 ± 5 | 39 ± 6 |
| 0.2 | 45 ± 2 | 42 ± 2 |
| 0.5 | 46 ± 2 | 45 ± 2 |
| 1.0 | 45 ± 2 | 43 ± 2 |

Applications of the Present Hydrogel Foams
Long-term Oral Drug Delivery System

Of the many routes of drug delivery, the oral administration has been considered to be the most convenient means to introduce drugs into the systemic circulation. The oral route is the preferred route for drug delivery except for those drugs susceptible to degradation by digestive enzymes or when extremely rapid onset of action is desired.

Recent innovations in the design of oral dosage forms permit controlled release of drugs. Despite these advances, the development of oral controlled release dosage forms has been slow and the formulation of once-a day oral dosage forms for most drugs has yet to be achieved. The major obstacle to achieving the once-a-day dosing arises from the fact that a dosage form passes through the stomach and small intestine in a relatively short period of time, thus limiting the exposure time of the drug to different segments of the gastrointestinal (GI) tract. Regardless of whether the in vivo release of the drug formulations is constant, the extent of drug absorption will be related to the residence time the dosage form spends within each segment of the gut.

The intestinal transit time is especially important for the absorption of poorly soluble drugs or compounds which are absorbed primarily from the upper segment of the gut. It has been reported that transit time from mouth to the cecum is approximately 3–7 h, and transit through the whole gut varies from 22 to 120 h. The time interval from mouth to cecum is too short for controlled release delivery systems which are designed to deliver drugs for more than 12 h and up to 24 h, unless the drug is to be absorbed from the large intestine.

Most drugs are absorbed from the upper portion of the small intestine, dudodenum and jejunum, and thus it is desirable to decrease the rate of transit past this point by retaining the dosage form in the stomach. Several approaches have been taken to prolong the gastric retention time of dosage forms. First, the density of drug delivery systems was altered in an attempt to make the dosage forms either float on the gastric juice or fall against the wall of the stomach and become trapped in the mucous lining, and thereby delay the gastric emptying. Although these devices were successful to some extent in increasing the gastric residence time, the increase in resident time is still too short for the controlled release dosage forms. In fact, it has been shown that specific gravity has only a minor effect on the gastric emptying of these devices. The major factor determining the gastric emptying of single dosage forms was the presence of food rather than the density of the dosage forms.

Mucoadhesive polymers have also been used as platforms to attach and hold dosage forms to the gastric mucosa and retard the gastric emptying. It has been reported that mucoadhesives may stay attached to the gastric mucus layer for a prolonged period of time until their spontaneous removal from the surface by various factors including natural mucus turnover. This approach, however, has not been successful because the mucoadhesives available so far interact nonspecifically with soluble mucins and proteins which are present in the gastric juice and subsequently lose their ability to attach to the mucus layer.

The shape of the drug delivery system has been designed to enhance gastric retention time. These devices typically are designed to either unfold wings or unroll upon contact with fluid in the gastric environment to accomplish enhanced gastric retention. Although this approach has been successful in animals, in humans the dosage form has to be removed from the stomach and from the body after its use. There is thus a need to solubilize the gastric retention devices after its use in addition to accomplishing the retention in the stomach.

Hydrogels have been used widely in the development of controlled drug delivery systems. Recently, biodegradable hydrogels which swell in the stomach were used as a platform for long-term oral drug delivery. It has been reported that hydrogels can be administered to dogs such that the hydrogels remained in the stomach for up to 60 h. One of the key factors that maintained the hydrogel in the stomach is the large size of the swollen hydrogel. One of the difficulties in the use of the hydrogel system was that the hydrogel did not swell fast enough to be retained in the stomach in the presence of housekeeper waves. Hydrogels, typically take hours to swell, especially if the size of the dried hydrogel is that of ordinary tablets. The problems associated with slow swelling of hydrogels can be overcome using the hydrogel foams of the present invention. Suitable pharmacological/pharmaceutical materials that can be delivered through the use of hydrogel foams are described in U.S. Pat. No. 4,178,361 the disclosure of which is expressly incorporated herein by reference. Hydrogel foam based oral dosage forms of such orally effective agents can be prepared for example by swelling the foams in solutions of such agents thereafter drying the rehydrated foam to provide a hydrogel foam impregnated with the active agent.

Gastric Retention Device for Diet Control

In addition to drug delivery, the hydrogel foams can be used to control the appetite of healthy people who desire to reduce the volume of food they take. The presence of bulky hydrogel foams will reduce the space in the stomach and thus the amount of food that can be ingested. The extended presence of hydrogel foams in the stomach will slow down the emptying of food into the intestine. Thus, the hydrogel foams of the present invention can also be used as a therapy for obesity. The weight loss will be especially important to persons with noninsulin-dependent diabetes mellitus, since they frequently are no longer diabetic after weight loss.

We claim:

1. An absorbent hydrogel foam comprising a solid phase comprising a surfactant and a polymer or copolymer of a free radical polymerizable hydrophilic olefin monomer crosslinked with about 0.1 to about 10% by weight of a crosslinking agent having at least two alkenyl groups; and a gas phase, wherein the ratio of the volume of the gas phase to the volume of the solid phase is at least one.

2. The hydrogel foam of claim 1, wherein said surfactant is a protein.

3. The hydrogel foam of claim 1, wherein said crosslinking agent is biodegradeable.

4. The hydrogel foam of claim 1, wherein a volume of said foam, having a size greater than 1 mm in its smallest dimension, exhibits a water swelling ratio of at least 15 within one hour of contact with an aqueous solution.

5. The hydrogel foam of claim 1, wherein a volume of said foam, having a size greater than 1 mm in its smallest dimension, exhibits at least 50% of its maximum swelling ratio within one hour of contact with an aqueous solution.

6. A method for producing a water absorbent hydrogel foam matrix, said method comprising the steps of polymerizing at least one hydrophilic olefin monomer compound in an aqueous solution, said aqueous solution comprising about 0.1 to about 10% by weight of a crosslinking agent having at least two alkenyl groups and a surfactant;

introducing gas into the monomer solution during said polymerization step to form a foamed polymer matrix hydrogel foam;

contacting the hydrogel foam with a volatile water miscible solvent; and drying said hydrogel foam.

7. The method of claim 6, wherein the step of drying comprises contacting the hydrogel foam with an absorbent material followed by air drying the matrix at room temperature.

8. The method of claim 7 further comprising the step of drawing warmed air across the hydrogel foam surface during the step of drying.

9. A water swellable hydrogel foam formed as a macroporous solid comprising a foam stabilizing agent and a polymer or copolymer of a free radical polymerizable hydrophilic olefin monomer crosslinked with about 0.1 to about 10% by weight of a crosslinking agent having at least two alkenyl groups, wherein a volume of said hydrogel foam, having a size greater than 2 mm in its smallest dimension, exhibits a water swelling ratio of at least 15 within one hour of contact with an aqueous solution.

10. The hydrogel foam of claim 9 wherein the crosslinking agent is biodegradable.

11. A water swellable hydrogel foam formed as a macroporous solid comprising a surfactant and polymer or copolymer of a free radical polymerizable hydrophilic olefin monomer crosslinked with about 0.1 to about 10% by weight of a crosslinking agent having at least two alkenyl groups, wherein a volume of said hydrogel foam, having a size greater than 1 mm in its smallest dimension, exhibits greater than 50% of its maximum swelling ratio within one hour of contact with an aqueous solution.

12. The hydrogel foam of claim 11 wherein the crosslinking agent is biodegradable.

* * * * *